(12) United States Patent
Schlaf et al.

(10) Patent No.: US 7,112,816 B2
(45) Date of Patent: Sep. 26, 2006

(54) CARBON NANOTUBE SENSOR AND METHOD OF PRODUCING THE SAME

(75) Inventors: Rudiger Schlaf, Lutz, FL (US); Shekhar Bhansali, Tampa, FL (US)

(73) Assignee: University of South Flordia, Tampa, FL (US)

( * ) Notice: Subject to any disclaimer, the term of this patent is extended or adjusted under 35 U.S.C. 154(b) by 329 days.

(21) Appl. No.: 10/413,621

(22) Filed: Apr. 14, 2003

(65) Prior Publication Data

US 2003/0218224 A1 Nov. 27, 2003

Related U.S. Application Data

(60) Provisional application No. 60/319,183, filed on Apr. 12, 2002.

(51) Int. Cl.
*H01L 29/772* (2006.01)

(52) U.S. Cl. ............ 257/24; 257/20; 257/E29.07; 977/748; 977/938

(58) Field of Classification Search ........... 257/E51.04
See application file for complete search history.

(56) References Cited

U.S. PATENT DOCUMENTS

| | | | |
|---|---|---|---|
| 6,146,227 A | 11/2000 | Mancevski | |
| 6,159,742 A * | 12/2000 | Lieber et al. | 436/164 |
| 6,346,189 B1 * | 2/2002 | Dai et al. | 205/766 |
| 6,445,006 B1 | 9/2002 | Brandes et al. | |
| 6,457,350 B1 | 10/2002 | Mitchell et al. | |
| 6,492,261 B1 | 12/2002 | Gavish et al. | |
| 2003/0015774 A1 | 1/2003 | Auburger et al. | |
| 2003/0059968 A1 | 3/2003 | Cheng et al. | |
| 2003/0143327 A1 | 7/2003 | Schlaf et al. | |
| 2004/0022943 A1 | 2/2004 | Schlaf | |

FOREIGN PATENT DOCUMENTS

EP 1 129 990 A1 9/2001

OTHER PUBLICATIONS

Merkulov et al, APL vol. 79 No. 18, Oct. 29, 2001, pp. 2970-2972 "Alignment . . . deposition".*
Joselevich et al, Nano Letters vol. 2 No. 10 pp. 1137-1141 "Vectorial . . . Nanotubes".*
Lagel et al, Material Res. Soc. Symp. Proc. vol. 858E HH13.3.1 "Integration . . . Structures".*

(Continued)

*Primary Examiner*—Jerome Jackson
(74) *Attorney, Agent, or Firm*—Howard & Howard Attnys.

(57) ABSTRACT

A carbon nanotube sensor and a method of producing the carbon nanotube sensor are disclosed. The sensor detects small particles and molecules. The sensor includes a gate, a source and a drain positioned on the gate, and a carbon nanotube grown from a catalytic material and extending from one of the source and the drain. The method includes the step of functionalizing an end of the carbon nanotube with a receptor. As such, the carbon nanotube is receptive to the small particles and molecules. The carbon nanotube is driven at a resonance, and the resonance of the carbon nanotube is measured when the end of the carbon nanotube is free of the small particles and the molecules. The method includes monitoring for a change in the resonance to detect the association of the small particles and molecules with the end of the carbon nanotube.

28 Claims, 1 Drawing Sheet

OTHER PUBLICATIONS

Chin Li Cheung, Jason H. Hafner, and Charles M. Lieber, "Carbon nanotube atomic force microscopy tips: Direct growth by chemical vapor deposition and application to high-resolution imaging"; Apr. 11, 2000. PNAS, vol. 97, No. 8, pp. 3809-3813.

Chin Li Cheung, Jason H. Hafner, Teri W. Odom, Kyoungha Kim, and Charles M. Lieber, "Growth and fabrication with single-walled carbon nanotube probe microscopy tips"; May 22, 2000; American Institute of Physics, Applied Physics Letters, vol. 76, No. 21, pp. 3136-3138.

Hongjie Dia, Jason H. Hafner, Andrew G. Rinzler, Daniel T. Colbert, and Richard E. Smalley, "Nanotubes as Nanoprobes in Scanning Probe Microscopy"; Nature 384, 147-151 (1996).

G. Nagy, M. Levy, R. Scarmozzino, R.M. Osgood, Jr. H. Dia, R.E. Smalley, C.A. Michaels, G.W. Flynn and G.F. McLane, "Carbon nanotube tipped atomic force microscopy for measurement of <100 nm etch morphology on semiconductors"; Jul. 27, 1998; American Institute of Physics, Applied Physics Letters, vol. 73, No. 4, pp. 529-531.

R. M.D. Stevens, N.A. Frederick, B.L. Smith, D.E. Morse, G.D. Stucky and P.K. Hansma, "Carbon nanotubes as probes for atomic force microscopy"; 2000 IOP Publishing ltd. Nanotechnology 11 (2000) 1-5. Printed in UK.

S.S. Wong, J.D. Harper, P.T. Lansbury, Jr. and C.M. Lieber, "Carbon Nanotube Tips: High-Resolution Probes for Imaging Biological Systems" J.Am. Chem Soc. 1998, 120, 603-604.

Copy of U.S. Appl. No. 10/310,219, filed Dec. 5, 2002.
Copy of U.S. Appl. No. 10/313,886, filed Dec. 6, 2002.
Copy of U.S. Appl. No. 10/413,597, filed Apr. 14, 2003.
Copy of U.S. Appl. No. 10/413,598, filed Apr. 14, 2003.

* cited by examiner

CARBON NANOTUBE SENSOR AND METHOD OF PRODUCING THE SAME

RELATED APPLICATIONS

This patent application claims priority to and all advantages of U.S. Provisional Patent Application No. 60/319,183, which was filed on Apr. 12, 2002.

BACKGROUND OF THE INVENTION

1. Field of the Invention

The subject invention relates to a carbon nanotube sensor and a method of producing the sensor. More specifically, the carbon nanotube sensor detects small particles and molecules.

2. Description of the Related Art

Carbon-based nanotechnology has not, to date, been adequately applied across many industries to assist in the detection of various small particles and molecules. Small particles may include various pathogens, e.g. anthrax, proteins, and enzymes whereas the molecules may include various chemical agents such as sarin nerve gas. Carbon nanotube sensors have not been utilized in the medical, biological, and military industries to detect certain chemical or biological agents, harmful or otherwise.

Due to the limited application of carbon nanotube sensors throughout the many industries, it would be advantageous to provide a carbon nanotube sensor and a method of producing the sensor to assist in the detection of various small particles and molecules. Such a sensor would have significant application across a wide array of industries including, but not limited to, the medical, biological, and military industries.

SUMMARY OF THE INVENTION AND ADVANTAGES

A carbon nanotube sensor and a method of producing the carbon nanotube sensor are disclosed. The sensor detects a small particle or molecule. To accomplish this, the sensor includes a gate, a source and a drain positioned on the gate, and a carbon nanotube. The carbon nanotube is grown from a catalytic material and extends from one of the source and the drain.

The method includes the step of functionalizing an end of the carbon nanotube. More specifically, a functional receptor is disposed at an end of the carbon nanotube such that the carbon nanotube, now functionalized, is receptive to at least one of the small particle and the molecule. Next, the functionalized carbon nanotube is driven in a resonance, and then the resonance of the functionalized carbon nanotube is measured when the end of the functionalized carbon nanotube is free of the small particle and the molecule. The method further includes the step of monitoring for a change in the resonance. The carbon nanotube resonates at a first resonance frequency when the functional receptor at the end of the carbon nanotube is free of the small particle and the molecule, and the carbon nanotube resonates at a second resonance frequency that is different from the first resonance frequency when at least one of the small particle and the molecule is associated with the functional receptor at the end of the carbon nanotube. Monitoring for the change in the resonance, detects the association of at least one of the small particle and the molecule with the end of the functionalized carbon nanotube.

Accordingly, the subject invention provides a method of producing a carbon nanotube sensor that is assists in the detection of various small particles and molecules, especially the small particles and molecules that are important to detect in the medical, biological, and military industries. The method of the subject invention also enables mass production of the carbon nanotube sensors in a fashion that is similar to the production of conventional integrated circuits by permitting a large array of millions of single carbon nanotube sensors.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 2A:
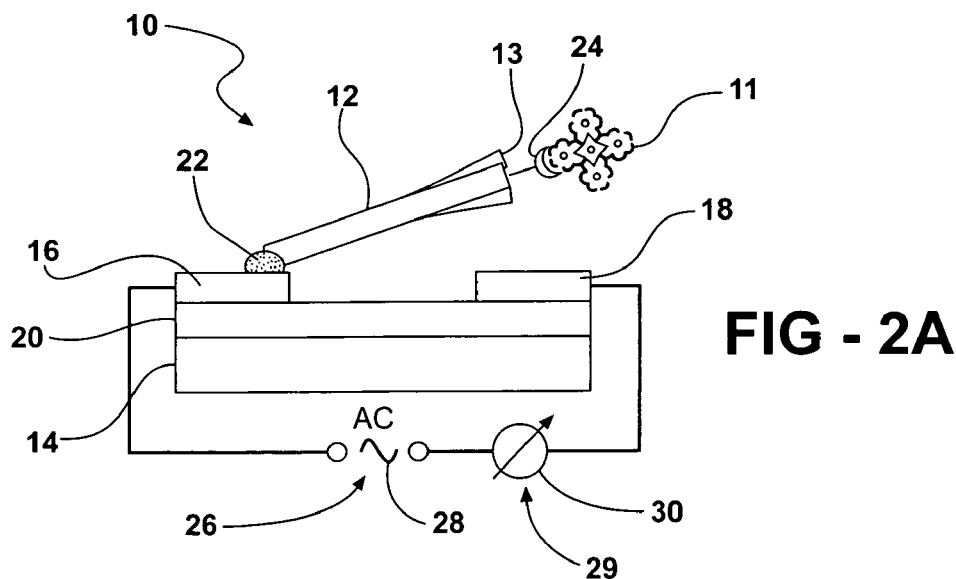
FIG. 2A is a side view of the sensor of FIG. 1A resonating at a second resonance frequency because at least one of the small particle and the molecule is associated with the functional receptor at the end of the carbon nanotube.

Referring to the Figures, wherein like numerals indicate like or corresponding parts throughout the several views, a method for producing a carbon nanotube (CNT) sensor 10 and the CNT sensor 10 itself are disclosed. The CNT sensor 10 detects a small particle or molecule. Both the small particle and molecule are represented by the number 11 FIG. 2A. The CNT sensor 10 may detect a plurality of small particles 11 and/or a plurality of molecules 11.

The method of the subject invention enables mass production of the CNT sensor 10 or an entire plurality of the CNT sensors 10, similar to the mass production of integrated circuits. This mass production is enabled by the growth process for a carbon nanotube 12, which is a critical component of the CNT sensor 10. This growth process is described additionally below. Furthermore, the CNT sensor 10 produced according to the method of the subject invention may further be incorporated into other devices, which may or may not make use of nanotechnology beyond the CNT sensor 10. For example, the CNT sensor 10 of the subject invention can be integrated with conventional integrated circuits which allows placing necessary electronic devices such as current amplifiers on the same chip thereby enabling large arrays of such CNT sensors 10 with millions of single units.

Figure 1A:
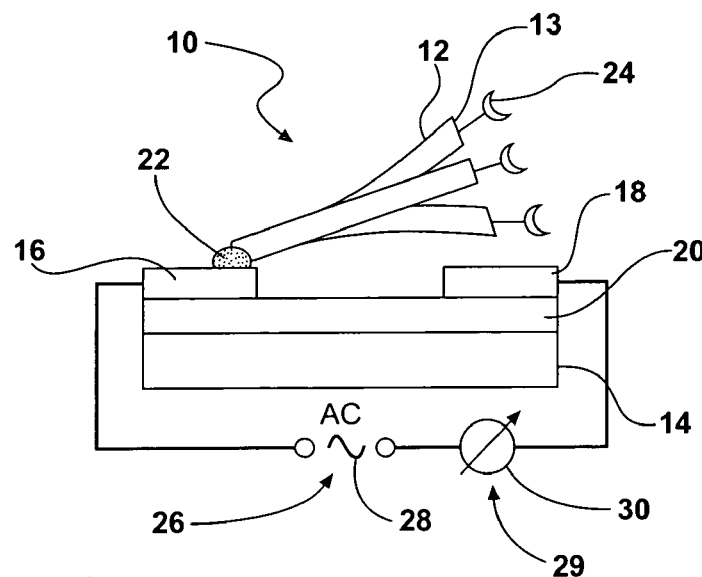
FIG. 1A is a side view of carbon nanotube sensor produced according to the method of the subject invention resonating at a first resonance frequency because a functional receptor at an end of the carbon nanotube is free of the small particle and the molecule.

The CNT sensor 10 includes a gate 14 and a source 16 and a drain 18. Both the source 16 and the drain 18 are positioned on the gate 14. As particularly disclosed in FIGS. 1A and 2A, the gate 14 is coated with a gate oxide layer 20. The CNT sensor 10 also includes the carbon nanotube 12 that is grown from a catalytic material 22. Preferably, the catalytic material 22 is selected from the group consisting of nickel, cobalt, iron, and combinations thereof.

The carbon nanotube 12 extends from one of the source 16 and the drain 18. That is, the carbon nanotube 12 can extend from either the source 16 or the drain 18 without varying the scope of the subject invention. Preferably, and as disclosed in the Figures, the carbon nanotube 12 extends from the source 16.

To extend from either the source 16 or the drain 18, the carbon nanotube 12 can be grown to extend from either the source 16 or the drain 18, as described below, or the carbon nanotube 12 can first be grown elsewhere and then subsequently attached to either the source 16 or the drain 18. However, it is preferred that the carbon nanotube 12 is grown to extend from either the source 16 of the drain 18, as described immediately below, and is not subsequently attached.

The catalytic material 22 is deposited onto one of the source 16 and the drain 18, preferably it is deposited on the source 16 such that the carbon nanotube 12 extends from the source 16. However, in alternative embodiments, the catalytic material 22 may be deposited on the drain 18 such that the carbon nanotube 12 extends from the drain 18. Preferably, the depositing of the catalytic material 22 is carried out using a focused ion beam (FIB) deposition technique or other similar patterning techniques with high resolution. The FIB deposition technique is understood by those skilled in the art. The FIB deposition technique uses an ion beam to deposit the catalytic material 22 onto the source 16 with surgical precision.

Next, the catalytic material 22 is subjected to, i.e. exposed to, chemical vapor deposition (CVD) to initiate growth of the carbon nanotube 12 such that the carbon nanotube 12 extends from one of the source 16 and the drain 18, preferably from the source 16, prior to functionalizing an end 13 of the carbon nanotube 12. The step of functionalizing the end of the carbon nanotube 12 is described additionally below. CVD is a chemical reaction that transforms gaseous molecules, called precursors, into a solid material, in the form of thin film. Many different precursors may be utilized with the subject invention. Common precursors include, but are not limited to, hydrides, halides, metal-organics such as metal alkyls, metal alkoxides, metal dialkylamides, metal diketonates, or metal carbonyls, and combinations thereof. For forming the carbon nanotube 12 of the CNT sensor 10, it is understood that the source 16 of carbon may be any organic compound, such as acetylene.

The CVD is carried out in a reactor. Most reactors include gas and vapor delivery lines, a reactor main chamber having a hot wall and a cold wall. The reactor also includes a sensor loading and unloading assembly for positioning the CNT sensor 10 within the reactor. The reactor also includes at least one energy source. Typical examples of energy sources include resistive heating, radiant heating, and inductive heating. Resistive heating includes energy from a tube furnace or a quartz tungsten halogen lamp. Radiant heating provides energy from radio-frequency and inductive heating provided energy from a laser as a thermal energy source. Yet another energy source is photo energy from an UV-visible light laser.

The products from the CVD include a solid and a gas product. The solid product is the growth of the carbon nanotube 12. The gas products are volatile byproducts and are always formed. The gas products generated in CVD processes are usually hazardous and must be disposed of accordingly.

Another type of CVD is plasma enhanced CVD (PECVD). PECVD is performed in a reactor at temperatures up to ~1000° C. The deposited film is a product of a chemical reaction between the source gases supplied to the reactor. A plasma is generated in the reactor to increase the energy available for the chemical reaction at a given temperature. The system for carrying out the PECVD is similar to that described above for CVD.

Either a diameter of the carbon nanotube 12, or the number of walls present in the carbon nanotube 12, or both of these characteristics, can be varied by controlling an amount of the catalytic material 22 that is deposited onto the source 16 or the drain 18. Also, if the duration of the CVD is controlled, then the length of the carbon nanotube 12 can be varied. A suitable diameter and length of the carbon nanotube 12 are selected to be able to optimally detect a particular small particle 11 and/or a particular molecule 11.

In certain embodiments, it may be desirable to increase the rigidity of the carbon nanotube 12 that extends from the source 16 or the drain 18. To accomplish this, it is preferred that a suitable material, such as platinum, is deposited onto one of the source 16 and the drain 18 prior to deposition of the catalytic material 22. The platinum enhances the mechanical attachment of the carbon nanotube 12 to the source 16 or the drain 18 and enhances the lifetime of the carbon nanotube 12 in the CNT sensor 10. Preferably, the platinum is deposited using FIB deposition techniques.

Furthermore, the angle at which the carbon nanotube 12 grows relative to either the source 16 or the drain 18 can be controlled. To control this angle, it is possible to apply an electric field as the catalytic material 22 is subjected to CVD.

The method of the subject invention includes the step of functionalizing the end 13 of the carbon nanotube 12. More specifically, a functional receptor 24 is disposed at the end 13 of the carbon nanotube 12. As disclosed in the Figures, the functional receptor 24 is disposed at the end 13 of the carbon nanotube 12 that is opposite the point at which the carbon nanotube 12 extends from either the source 16 or the drain 18. As such, the functionalized carbon nanotube 12, specifically the functional receptor 24 at the end 13 of the carbon nanotube 12, is receptive to at least one of the small particle 11 and the molecule 11. In other words, the functional receptor 24 enables the small particle 11 and/or the molecule 11 to attach to the carbon nanotube 12. It is to be understood that the particular functional receptor 24 is not critical to the novelty of the subject invention. That is, the functional receptor 24 can vary depending on the size and type of the small particle 11 and/or the molecule 11 that the CNT sensor 10 is designed to receive or attach to. Therefore, the step of functionalizing the end 13 of the carbon nanotube 12 incorporates selectivity into the CNT sensor 10 because the functional receptor 24 disposed at the end 13 of the carbon nanotube 12 can be customized to be receptive to any size and type of small particle 11 or molecule 11. As one example of customization, the end 13 of the carbon nanotube 12 may be conditioned with a selected chemical that is only reactive with a particular small particle 11 or molecule 11.

It is also to be understood that the end 13 of the carbon nanotube 12 can be functionalized by any mechanism known to those skilled in the art. Examples of suitable mechanisms include, but are not limited to: (1) chemically modifying the end 13 of the carbon nanotube 12 to be receptive to at least one of the small particle 11 and the molecule 11; (2) depositing certain molecules on the end 13 of the carbon nanotube 12 that are receptive to at least one of the small particle 11 and the molecule 11; and (3) placing the end 13 of the carbon nanotube 12 into a solution of certain molecules that are receptive to at least one of the small particle 11 and the molecule 11. For the second (2) mechanism, it is preferred that the certain molecules are deposited on the end 13 of the carbon nanotube 12 in a vacuum. These certain molecules are not to be confused with the molecule 11 that is detected with the CNT sensor 10 of the subject invention. Prior to depositing any of the certain molecules on the end 13 of the carbon nanotube 12, the certain molecules are preferably incorporated into a solution and then ionized by subjecting the solution to such mechanisms as electron ionization, electrospray ionization, and matrix-assisted laser desorption/ionization. For the third (3) mechanism, the most preferred manner in which to place the end 13 of the carbon nanotube 12 into such a solution is by simple dipping.

After the end 13 of the carbon nanotube 12 has been functionalized, the method further includes the step of driving the functionalized carbon nanotube 12 in a resonance. It is to be understood that the functionalized carbon nanotube 12 can be driven into the resonance by a wide variety of mechanisms. No matter what the mechanism, the functionalized carbon nanotube 12 resonates at a first resonance frequency, as disclosed in FIG. 1A, when the end 13 of the functionalized carbon nanotube 12, specifically the functional receptor 24 at the end 13 of the carbon nanotube 12, is free of the small particle 11 and the molecule 11. This first resonance frequency is illustrated by the three different positions for the functionalized carbon nanotube 12 in FIG. 1A. On the other hand, as particularly disclosed in FIG. 2A, the functionalized carbon nanotube 12 resonates at a second resonance frequency that is different from the first resonance frequency, when at least one of the small particle 11 and the molecule 11 is associated with the functionalized carbon nanotube 12, specifically with the functional receptor 24 at the end 13 of the carbon nanotube 12. This second resonance frequency is illustrated by the three different positions for the functionalized carbon nanotube 12 in FIG. 2A.

As a result of the resonance of the functionalized carbon nanotube 12, when the end 13 of the functionalized carbon nanotube 12 is free of the small particle 11 and the molecule 11, the resonance of the functionalized carbon nanotube 12 can be measured. Next, the method monitors for a change in the resonance. In other words, the method detects the existence in a change in the resonance. As one example, the change in the resonance can be indicated by a change from the first resonance frequency to the second resonance frequency being greater than some predetermined threshold. The change in the resonance enables the CNT sensor 10 to detect the association of at least one of the small particle 11 and the molecule 11 with the end 13 of the functionalized carbon nanotube 12. In other words, once the resonance changes, this indicates that either a small particle 11 or a molecule 11 has attached to the functional receptor 24.

In the most preferred embodiment of the subject invention, as illustrated throughout the Figures, an electrical source 26, most preferably an AC voltage source 28, applies an AC voltage to resonate the functionalized carbon nanotube 12. More specifically, the AC voltage is applied between the functionalized carbon nanotube 12 and the drain 18. This results in a capacitive current. Once the small particle 11 or molecule 11 attaches to the functional receptor 24 at the free end 13 of the carbon nanotube 12, the first resonance frequency changes due to the mass increase at the end 13 of the carbon nanotube 12. As a result, the amplitude of the oscillation will be weaker due to the phase shift occurring between the driving and resulting oscillation. This results in a reduction of the capacitive current that can be used as a detection signal.

Figure 1B:
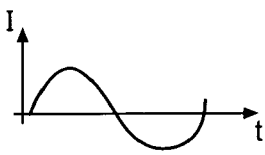
FIG. 1B is a graph illustrating a first current that is indicative of the first resonance frequency of the sensor resonating in FIG. 1A.
Figure 2B:
FIG. 2B is a graph illustrating a second current that is indicative of the second resonance frequency of the sensor resonating in FIG. 2A.

In this embodiment with the AC voltage, one manner in which to measure the first resonance of the functionalized carbon nanotube 12 is to measure a first current, as is illustrated in FIG. 1B (Current vs. Time). More specifically, the first current, which is indicative of the first resonance frequency of the functionalized carbon nanotube 12, exists when the end 13 is free of the small particles 11 and molecules 11. By measuring the first current, the step of monitoring for the change in the resonance actually monitors for a change from the first current to a second current that is less than the first current. The second current, which is indicative of the second resonance frequency, is illustrated in FIG. 2B (Current vs. Time). This second current exists when at least one of the small particle 11 and the molecule 11 is associated with the end 13 of the functionalized carbon nanotube 12 due to the mass of either the small particle 11 or the molecule 11 that is attached to the functional receptor 24 causing the functionalized carbon nanotube 12 to resonate further away from the drain 18. To measure the first and second currents, and also to measure any change from the first current to the second current, the CNT sensor 10 may include a detection mechanism 29. The most preferred detection mechanism 29 is an amp meter 30 as disclosed in the Figures.

Obviously, many modifications and variations of the present invention are possible in light of the above teachings. The invention may be practiced otherwise than as specifically described within the scope of the appended claims.

What is claimed is:

1. A method of producing a carbon nanotube sensor for detection of a small particle or molecule, wherein the sensor includes a gate, a source and a drain positioned on the gate, and a carbon nanotube grown from a catalytic material and extending from one of the source and the drain, said method comprising the steps of:

functionalizing an end of the carbon nanotube such that the functionalized carbon nanotube is receptive to at least one of the small particle and the molecule;

driving the functionalized carbon nanotube in a resonance;

measuring the resonance of the functionalized carbon nanotube when the end of the functionalized carbon nanotube is free of the small particle and the molecule; and monitoring for a change in the resonance to detect the association of at least one of the small particle and the molecule with the end of the functionalized carbon nanotube.

2. A method as set forth in claim 1 further comprising the steps of:

depositing the catalytic material onto one of the source and the drain; and subjecting the catalytic material to chemical vapor deposition to initiate growth of the carbon nanotube such that the carbon nanotube extends from one of the source and the drain, prior to functionalizing the end of the carbon nanotube.

3. A method as set forth in claim 2 wherein the step of depositing the catalytic material onto one of the source and the drain is further defined as depositing the catalytic material onto the source.

4. A method as set forth in claim 3 wherein the step of subjecting the catalytic material to chemical vapor deposition is further defined as subjecting the catalytic material to chemical vapor deposition to initiate growth of the carbon nanotube such that the carbon nanotube extends from the source.

5. A method as set forth in claim 2 wherein the step of depositing the catalytic material onto one of the source and the drain is further defined as depositing a catalytic material selected from the group consisting of nickel, cobalt, iron, and combinations thereof.

6. A method as set forth in claim 2 wherein the step of subjecting the catalytic material to chemical vapor deposition comprises the step of transforming a gaseous precursor selected from the group consisting of hydrides, halides, metal-organics, and combinations thereof into a solid material.

7. A method as act forth in claim 2 wherein the step of subjecting the catalytic material to chemical vapor deposition is further defined as subjecting the catalytic material to plasma enhanced chemical vapor deposition.

8. A method as set forth in claim 2 wherein the step of depositing the catalytic material onto one of the source and the drain is further defined as depositing the catalytic material onto one of the source and the drain using focused ion beam deposition.

9. A method as set forth in claim 2 wherein the step of depositing the catalytic material onto one of the source and the drain comprises the step of controlling an amount of the catalytic material that is deposited onto one of the source and the drain to vary at least one of a diameter of the carbon nanotube and a number of walls present in the carbon nanotube.

10. A method as set forth in claim 2 wherein the step of subjecting the catalytic material to chemical vapor deposition comprises the step of controlling a duration of the chemical vapor deposition to vary a length of the carbon nanotube.

11. A method as set forth in claim 2 further comprising the step of increasing the rigidity of the carbon nanotube that extends from one of the source and the drain.

12. A method as set forth in claim 11 wherein the step of increasing the rigidity of the carbon nanotube is further defined as depositing platinum onto one of the source and the drain prior to deposition of the catalytic material.

13. A method as set forth in claim 1 wherein the step of functionalizing the end of the carbon nanotube is further defined as chemically modifying the end of the carbon nanotube to be receptive to at least one of the small particle and the molecule.

14. A method as set forth in claim 1 wherein the step of functionalizing the end of the carbon nanotube is further defined as depositing molecules on the end of the eaten nanotube that are receptive to at least one of the small particle and the molecule.

15. A method as set forth in claim 1 wherein the step of functionalizing the end of the carbon nanotube is further defined as placing the end of the carbon nanotube into a solution of molecules that are receptive to at least one of the small particle and the molecule.

16. A method as set forth in claim 1 wherein the step of driving the functionalized carbon nanotube in the resonance is further defined as applying an AC voltage between the functionalized carbon nanotube and the drain such that the functionalized carbon nanotube resonates at a first resonance frequency when the end of the functionalized carbon nanotube is free of the small particle and the molecule.

17. A method as set forth in claim 16 wherein the step of monitoring for the change in the resonance is further defined as monitoring for a change from the first resonance frequency to a second resonance frequency that is different than the first resonance frequency, wherein the second resonance frequency indicates that at least one of the small particle and the molecule is associated with the end of the functionalized carbon nanotube.

18. A method as set forth in claim 16 wherein the step of measuring the resonance of the functionalized carbon nanotube is further defined as measuring a first current that is indicative of the first resonance frequency of the functionalized carbon nanotube when the end is free of the small particles and molecules.

19. A method as set forth in claim 18 wherein the step of monitoring for the change in the resonance is further defined as monitoring for a change from the first current to a second current that is less than the first current, wherein the second current indicates that at least one of the small particle and the molecule is associated with the end of the functionalized carbon nanotube.

20. A method as set forth in claim 2 further comprising the step of controlling an angle that the carbon nanotube grows at relative to one of the source and the drain.

21. A method as set forth in claim 20 wherein the step of controlling the angle that the carbon nanotube grows at is further defined as applying an electric field as the catalytic material is subjected to chemical vapor deposition.

22. A carbon nanotube sensor for detection of a small particle or molecule, said sensor comprising:

a gate;

a source and a drain positioned on said gate;

a carbon nanotube extending from one of said source and said drain and being grown from a catalytic material deposited on one of said source and said drain;

a functional receptor disposed at an end of said carbon nanotube such that said carbon nanotube is receptive to at least one of the small particle and the molecule;

wherein said carbon nanotube resonates at a first resonance frequency when said functional receptor at said end of said carbon nanotube is free of the small particle and the molecule, and said carbon nanotube resonates at a second resonance frequency that is different from said first resonance frequency when at least one of the small particle and the molecule is associated with said functional receptor at said end of said carbon nanotube.

23. A sensor as set forth in claim 22 wherein said catalytic material is selected from the group consisting of nickel, cobalt iron, and combinations thereof.

24. A sensor as set forth in claim 22 further comprising an electrical source for resonating said carbon nanotube.

25. A sensor as set forth in claim 24 wherein said electrical source is further defined as an AC voltage source such that a first current can be measured when said functional receptor is free of the small particle and the molecule and said carbon nanotube is resonating at said first resonance frequency, and a second current can be measured when at least one of the small particle and the molecule is associated with said functional receptor and said carbon nanotube is resonating at said second resonance frequency.

26. A sensor as set forth in claim 25 further comprising a detection mechanism for measuring a change from said first current to said second current.

27. A sensor as set forth in claim 26 wherein said detection mechanism is further defined as an amp meter.

28. A sensor as set forth in claim 22 wherein said carbon nanotube is grown by subjecting said catalytic material to chemical vapor deposition.

* * * * *

UNITED STATES PATENT AND TRADEMARK OFFICE
CERTIFICATE OF CORRECTION

PATENT NO. : 7,112,816 B2 Page 1 of 1
APPLICATION NO. : 10/413621
DATED : September 26, 2006
INVENTOR(S) : Rudiger Schlaf et al.

It is certified that error appears in the above-identified patent and that said Letters Patent is hereby corrected as shown below:

Column 7, line 15, after "as" delete "act" and insert therein -- set --.

Column 7, line 49, after "end of the" delete "eaten" and insert therein -- carbon --.

Column 8, line 46, after "cobalt" insert -- , --.

Signed and Sealed this

Nineteenth Day of December, 2006

JON W. DUDAS
*Director of the United States Patent and Trademark Office*